United States Patent [19]
Pillsbury

[11] Patent Number: 5,277,187
[45] Date of Patent: Jan. 11, 1994

[54] APPARATUS AND METHOD FOR IMPROVING THE PERFORMANCE OF AN AUTOMATIC BLOOD PRESSURE CUFF

[75] Inventor: Terrance L. Pillsbury, Keizer, Oreg.

[73] Assignee: SpaceLabs Medical, Inc., Redmond, Wash.

[21] Appl. No.: 774,990

[22] Filed: Oct. 15, 1991

[51] Int. Cl.$^5$ .............................................. A61B 5/02
[52] U.S. Cl. ................................. 128/682; 128/680; 128/681; 128/687; 128/677
[58] Field of Search ........................ 128/668, 677–690; 773; 417/313, 440; 606/201–203

[56] References Cited

U.S. PATENT DOCUMENTS

| | | |
|---|---|---|
| 4,072,171 | 2/1978 | Nakazawa . |
| 4,360,029 | 11/1982 | Ramsey, III . |
| 4,471,646 | 9/1984 | Walker . |
| 4,796,184 | 1/1989 | Bahr et al. ............... 364/413.03 |
| 5,054,494 | 10/1991 | Lazzaro et al. . |
| 5,137,024 | 8/1992 | Souma ........................ 128/685 |

Primary Examiner—David Isabella
Assistant Examiner—A. Zuttarelli
Attorney, Agent, or Firm—Seed and Berry

[57] ABSTRACT

An improved blood pressure measuring device includes a filter intermediate the pressure cuff and the bleed valve to prevent dust, dirt, and other debris from clogging the bleed valve and causing significant damage to the blood pressure measuring device. Further, a data processor assembly is operated in accordance with a method designed to compensate the blood pressure measurement for any resistance added to the pneumatic system as a result of the air filter. The data processor assembly further determines when the filter is clogged thereby indicating that the measurement can no longer be accepted as accurate and the device may be dangerous to the patient.

13 Claims, 4 Drawing Sheets

APPARATUS AND METHOD FOR IMPROVING THE PERFORMANCE OF AN AUTOMATIC BLOOD PRESSURE CUFF

TECHNICAL FIELD

The subject invention is directed toward automatic blood pressure cuffs and, more particularly, toward apparatus and method for improving the performance of a blood pressure cuff.

BACKGROUND OF THE INVENTION

Devices for automatically measuring blood pressure have become increasingly more popular. These devices typically allow a user to obtain quick blood pressure measurements without requiring a stethoscope or medical personnel. Further, due to the automated nature of these devices, the user does not need to participate in making the measurement except to put a conventional blood pressure cuff to his arm and start the measurement.

Most automated blood pressure measuring devices currently available rely upon a processor controlled pneumatic system to increase the pressure of the cuff enough to occlude the brachial artery. Once the cuff has attained a pressure sufficient to substantially occlude the brachial artery, the processor controlled pneumatic system slowly decreases the pressure of the cuff, either continuously or in increments. As the pressure of the cuff is reduced, the processor controlled pneumatic system records the pressure of the cuff at regular increments.

When the pressure in the cuff is reduced to systolic pressure, the flow of blood through the brachial artery beneath the cuff increases substantially. Following each contraction of the heart, blood flows through the brachial artery imparting pulsatile movement to the wall of the artery. This pulsatile movement causes minute changes in the pressure of the cuff, which changes are known as oscillometric pulses, and are recorded by the automatic blood pressure measuring device. As the pressure in the cuff is reduced toward zero, a table is created that contains values for the oscillometric pulse amplitude recorded at each cuff pressure. By processing the oscillometric pulses recorded in the table, the automatic blood pressure measuring device can determine relatively accurately the user's blood pressure.

Since these automatic blood pressure measuring devices are provided for substantially hands-free operation by unskilled users, it is necessary that they be constructed to operate properly with little or no maintenance. However, after prolonged use, dust, dirt, and other debris may collect in the pneumatic system of the device. This debris tends to clog the valves, and other devices of the pneumatic system, and substantially detract from proper operation of the automatic blood pressure measuring device. Accordingly, it is desirable to provide an automatic blood pressure measuring device including apparatus for preventing substantial buildup of dust, dirt, and other debris in the pneumatic system thereof.

Further, due to the resistance to gas of the pneumatic system, minor variations exist in the target pressure to which the data processor attempts to deflate the cuff and the actual pressure that is reached in the steady state. The effect of this resistance, and the difference between the target and actual pressures, is increased as dust, dirt, and other debris is accumulated in the pneumatic system.

Some systems have been developed with software that to provides a compensated target pressure, less than the target pressure by an offset value, so that the pressure is reduced to the compensated target pressure. As the system reaches equilibrium, and the pressure in the pneumatic system rises, the pressure in the pneumatic system approaches the target pressure so that the actual steady state pressure in the pneumatic system is substantially equal to the target pressure. However, these systems do not provide adequate compensation for extremely high resistances, which resistance cause the measurement to lose accuracy and may be dangerous to the patient. Therefore, it is desirable to provide method and apparatus for use with an automatic blood pressure measuring device that will eliminate loss of accuracy of the measurement and danger to the patient caused by extremely high resistances in the pneumatic system.

SUMMARY OF THE INVENTION

The present invention is directed toward a device for automatically measuring the blood pressure of a user. The device includes a fluid pressure assembly that is responsive to a fluid pressure signal for providing a fluid at a selectable pressure. The selectable pressure may be increased and/or decreased by varying the magnitude of the fluid pressure signal. The device also includes an inflatable cuff for selectively restricting the flow of blood in the user's body. The inflatable cuff is coupled to receive the fluid provided by the fluid pressure assembly, and to inflate and deflate with the respective increases and decreases in the selectable pressure, so that the amount of restriction to the flow of blood is varied by variation in the selectable pressure. A fluid conducting system is coupled intermediate the fluid pressure assembly and the inflatable cuff for conducting the fluid. The device also includes a pressure measuring assembly that is coupled to the fluid conducting system for providing a pressure signal indicative of the actual pressure of the fluid in the conduit. A data processor modulates the fluid pressure signal to vary the pressure in the fluid conducting system. The data processor is responsive to the pressure signal for stopping modulation to the fluid pressure signal when the pressure in the fluid conducting system equals the target pressure, and for measuring the difference between the target pressure that is desired and the steady state pressure attained in the fluid conducting system to determine an offset value. The data processor is constructed to combine the offset value with the target pressure to provide the fluid pressure signal.

In another presently preferred embodiment of the invention, the automatic blood pressure measuring device includes a filter for removing debris from the fluid conducted between the inflatable cuff and the fluid pressure assembly.

DETAILED DESCRIPTION OF THE INVENTION

Figure 1:
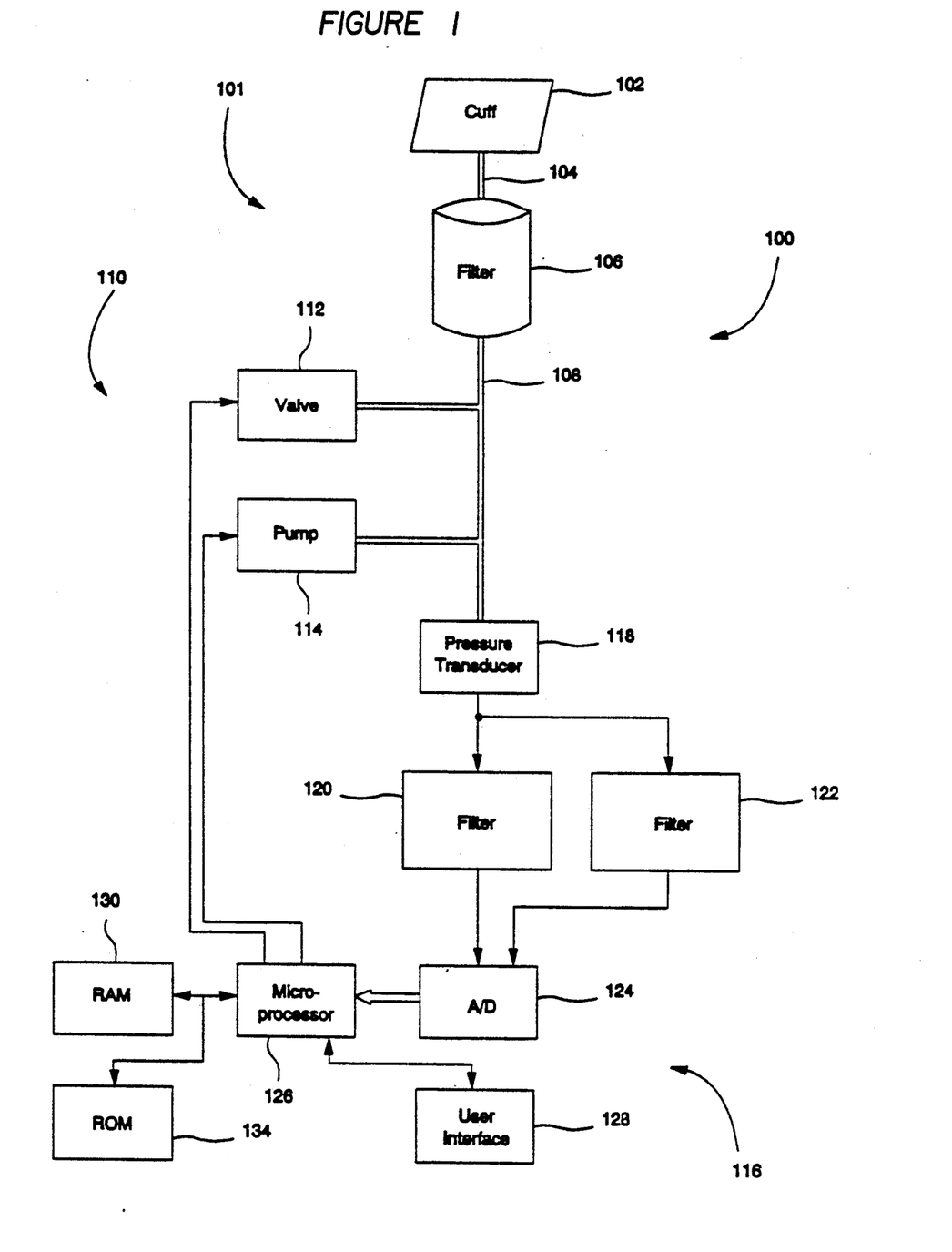
FIG. 1 is an illustrative block diagram of the automatic blood pressure measuring device that is the subject of the present invention.

An illustrative diagram of a blood pressure measuring device 100 is provided in FIG. 1. The blood pressure measuring device 100 includes a cuff 102 that is constructed to be placed upon the arm of a user for providing pressure to the user's arm. The cuff 102 is coupled to a pneumatic system 101 for receiving a fluid under pressure. When the pressure of the fluid supplied to the cuff 102 is increased, the pressure supplied to the arm of the user is similarly increased. Likewise, when the pressure of the fluid supplied to the cuff 102 is decreased, the pressure supplied to the user's arm by the cuff 102 is decreased. It will be apparent to those skilled in the art that, although the invention is described herein by reference to a cuff 102 that is constructed to be placed on the arm of a user, the invention is equally applicable to automatic blood pressure measuring devices that employ cuffs on other inflatable devices, that are constructed to be placed upon other body parts of a user.

The pneumatic system 101 includes a conduit 104, a filter 106, and a conduit 108. The pneumatic system 101 is provided for conducting the fluid under pressure to and from the inflatable cuff 102 to control the pressure supplied to the user's arm by the cuff. The filter 106 is coupled intermediate the conduit 104 and the conduit 108 for filtering dirt, dust, and debris of a predetermined size from the fluid that is conducted between the conduit 104 and the conduit 108. The construction of the filter 106 is discussed in more detail below by reference to FIG. 4.

The conduit 108 is coupled to a fluid pressure assembly 110 for receiving the fluid ultimately supplied to the cuff 102. The fluid pressure assembly 110 is preferably responsive to a fluid pressure signal for selectively increasing and decreasing the pressure of the fluid provided to the conduit 108. More particularly, the fluid pressure assembly may include a valve 112 and a pump 114. The valve 112 is responsive to a valve signal for enabling fluid to escape from the conduit 108 and thereby decrease the pressure of the fluid supplied to the cuff 102. Conversely, the pump 114 is responsive to a pump signal for providing additional fluid to the conduit 108 thereby increasing the pressure of the fluid supplied to the cuff 102. The combination of the valve signal and the pump signal make up the fluid pressure signal, discussed above.

In a presently preferred embodiment of the invention, the fluid that is supplied to the cuff 102 is air provided from the outside of the blood pressure assembly 110. The valve 112 and pump 114 comprise a conventional air valve and air pump responsive to electric signals for controlling the conduction of air between the conduit 108 and the outside of the fluid pressure assembly 110. Although the present invention is described by reference to an air valve 112 and air pump 114, those skilled in the art will appreciate that other devices may be substituted therefore without departing from the true scope and spirit of the subject invention. As an example, the fluid pressure assembly 110 may also be provided with a reservoir for receiving a liquid so that a liquid valve may be provided for conducting liquid from the conduit 108 to the reservoir and so that a liquid pump may be provided for conducting liquid from the reservoir to the conduit 108. Other arrangements for the fluid pressure assembly 110 will readily become apparent to those skilled in the art.

The conduit 108 is coupled to a fluid pressure controller 116 that is provided for controlling the operation of the fluid pressure assembly 110 and for performing the blood pressure measurement. The fluid pressure controller 116 includes a pressure transducer 118 that is coupled to the conduit 108 for sensing the pressure of the fluid in the conduit and for providing an electric signal indicative of the sensed pressure. In a presently preferred embodiment of the invention, the pressure transducer 118 is a conventional transducer that provides an electrical signal that increases and decreases with respective increases and decreases in the pressure of the fluid in the conduit 108. However, many other pressure transducers may be substituted therefor without departing from the scope of the present invention, as will be discussed in more detail below.

The pressure signal from the pressure transducer 118 is provided to first and second electrical filters 120 and 122. The first filter 120 is a low-pass filter provided for filtering oscillometric variations in pressure (or the A.C. component) from the pressure signal to provide a steady state pressure signal indicative of the average or steady state value of the pressure in the conduit 108. The second filter 122 is a band-pass filter centered about 2.4 Hz for filtering the steady state pressure (or the D.C. component) from the pressure signal to provide an oscillometric pressure signal indicative of the oscillometric pressure of the fluid contained in the conduit 108. As such, the steady state pressure signal is indicative of the pressure supplied to the cuff 102 by the fluid pressure assembly 110 and the oscillometric pressure signal is indicative of the pressure supplied to the cuff 102 by the contractions of the user's heart. Both the first and second filters 120 and 122 may be readily provided by those skilled in the art.

The steady state pressure signal and the oscillometric pressure signal are both provided to an analog to digital converter 124. The analog to digital converter comprises a conventional device that is constructed for converting an analog electrical signal to a digital value wherein the digital value is indicative of the magnitude of the analog signal. The analog to digital converter 124 converts both of the steady state pressure signal and the oscillometric pressure signal into digital signals that may be processed by the fluid pressure controller 116. The analog to digital converter 124 may be selected from a variety of conventional devices that are readily available to those skilled in the art.

The fluid pressure controller 116 further includes a microprocessor 126 that is constructed for receiving the digital steady state pressure signal and the digital oscillometric pressure signal and for providing the fluid pressure signal to control the steady state pressure of the fluid in the conduit 108. The microprocessor 126 is coupled to a user interface 128 that is provided for interfacing a user with the blood pressure measuring device 100. The user interface 128 may comprise apparatus for displaying information to the user, such as the determined blood pressure, and for receiving information from the user, such as a start signal. As an example, the user interface 128 may comprise a digital display and one or more switches. Other possibilities for the user interface 128 will readily be apparent to those skilled in the art.

The microprocessor 126 is also coupled to a random access memory assembly 130 and a read-only memory assembly 134. The random access memory assembly 130 is provided for storing a plurality of values of the oscillometric pressure signal received from the analog to digital converter 124. The read-only memory 134 is provided for storing program instructions and data for controlling the operation of the microprocessor 126, as is known in the art. Both the random access memory assembly 130 and the read only memory assembly 134 may also include buffers, drivers, address decoders, and other circuitry for interfacing with the microprocessor 126. Although the random access memory assembly 130 and read-only memory assembly 134 are discussed herein for storing information for use by the microprocessor 126, other memory devices could be substituted therefor by those skilled in the art.

The microprocessor 126 may comprise any of a plurality of conventional microprocessors presently available to those skilled in the art. It will be apparent to those skilled in the art that although the fluid pressure controller 116 is described herein by reference to discreet devices, one or more of these devices may be integrated into a single package to perform the functions described above. Similarly, each of these devices may be integrated into a single device for controlling the operation of the blood pressure measuring device 100. Accordingly, those skilled in the art will recognize that many combinations may exist for the fluid pressure controller 116.

In accordance with the present invention, the fluid pressure controller 116 provides the fluid pressure signal to the fluid pressure assembly 110 to increase the pressure of the cuff 102 so that the brachial artery of the user is substantially occluded. Thereafter, the fluid pressure controller 116 varies the fluid pressure signal to control the fluid pressure assembly 110 to incrementally decrease the pressure in the pneumatic system 101, thereby decreasing the pressure supplied to the cuff 102. To decrease the pressure in the pneumatic system 101, the fluid pressure controller 116 varies the fluid pressure signal to open the valve 112 so that air is released from the conduit 108 and the pressure of the fluid in the conduit 108 is decreased. The fluid pressure controller 116 simultaneously measures the pressure in the conduit 108 and, when the pressure sensed in the conduit 108 equals the desired pressure, i.e., the pressure of the next increment, the fluid pressure controller 116 varies the fluid pressure signal to close the valve 112 so that the pressure of the fluid in the conduit 108 will stop changing. However, due to resistance in the pneumatic system 101, the pressure in the conduit 108 tends to continue to change for a brief period after the valve 112 is closed.

Figure 2A:
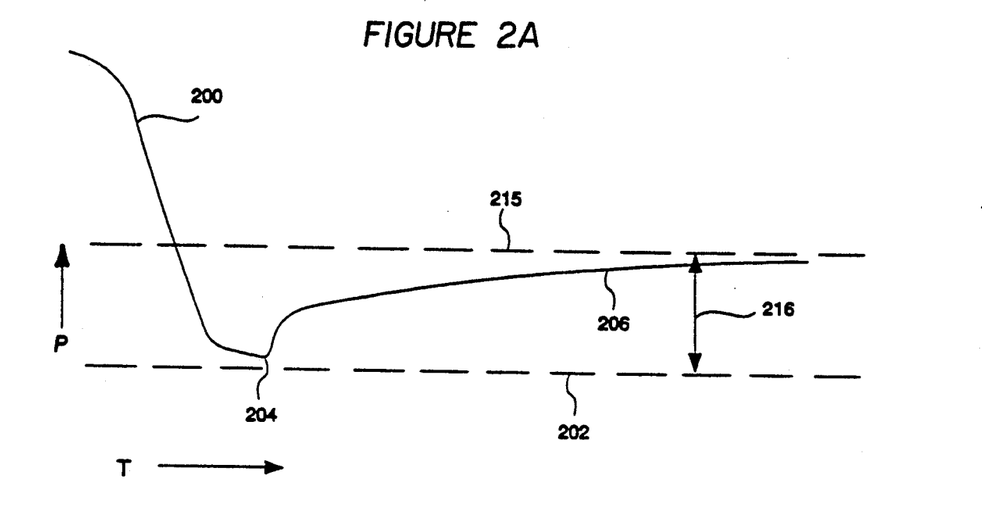
FIGS. 2A and 2B are graphs illustrating the increase in pressure of the pneumatic system of an automatic blood pressure measuring device resulting from resistance in the pneumatic system.
Figure 2B:
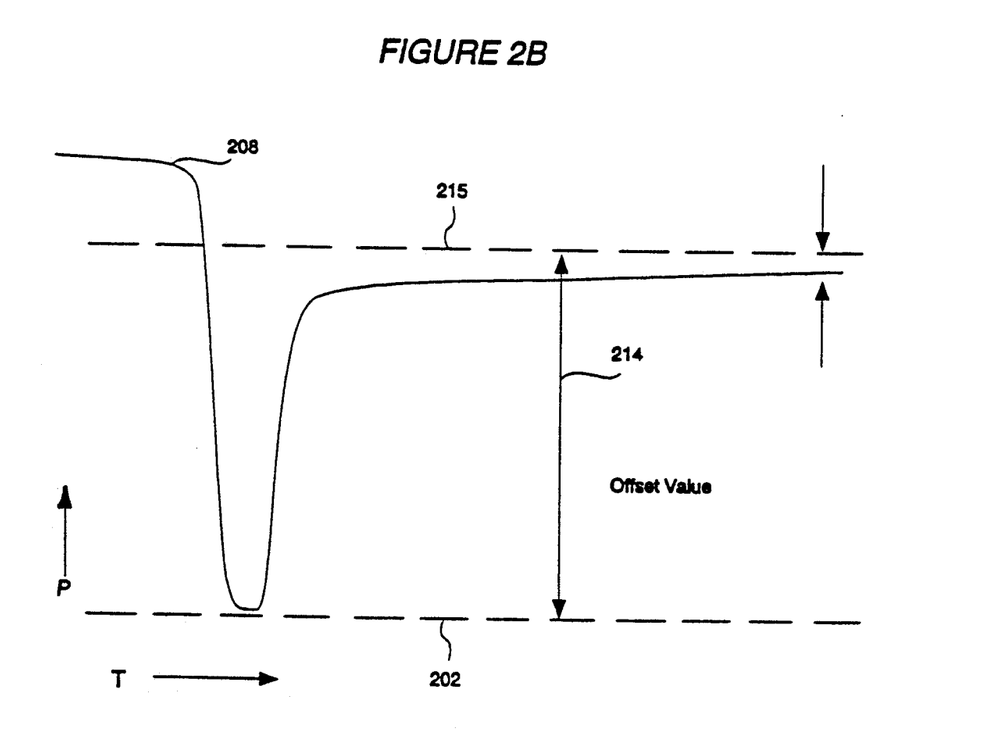

FIGS. 2A and 2B are graphs illustrating the effect of resistance of the pneumatic system 101 on the pressure in the conduit 108. FIG. 2A provides a graph illustrating the normal operation of the system when the filter 106 is not clogged. FIG. 2B illustrates the impaired operation when the filter 106 is partially clogged.

To compensate for the resistance in the pneumatic system 101, the fluid pressure controller 116 of the present invention determines an offset value. With reference to FIG. 2A, the solid line 200 indicates the pressure sensed in the conduit 108 by the pressure transducer 118. The graph incorporates a slight amount of software filtering that is commonly used in these applications. The dashed line 215 represents a target pressure, i.e., the desired pressure of the cuff, to which the fluid pressure controller 116 attempts to reduce the pressure of the fluid in the pneumatic system. However, in order to reach the final target 216, a compensated target pressure 202 must be calculated by subtracting an offset value 216 from the target pressure. When the controller senses a pressure equal to the compensated target pressure 202, it closes the valve 112, at 204. The pressure sensed at the fluid controller rises to the target pressure 215.

The behavior of the measured pressure 200 in the conduit 108 can be explained in the following manner. The pressure transducer 118 is located between the cuff 102 and the ambient room air. The pressure transducer is separated from the cuff by the pneumatic resistances of the filter 106 and conduit 104. The pressure transducer 118 is likewise separated from the ambient pressure by the pneumatic resistance of the valve 112. Therefore, while air is flowing through the system, the measured pressure falls between the cuff pressure and the ambient pressure. The pressure measured at 118 must be less than the pressure in the cuff 102. Once the valve 112 is closed, there is no longer any air flow. Without air flow, the pressure measured at the pressure transducer 118 is the same as that in the cuff 102. The rise in pressure that is actually measured is not as steep as might be expected for two reasons: (1) A small amount of software filtering is conventionally applied to the D.C. signal; and (2) The decrease in pressure has cooled the air in the cuff. The pressure rises as the cuff regains its steady state temperature.

FIG. 2B illustrates the impaired operation of the system when the filter 106 and conduit 104 becomes partially clogged. As the resistance of the filter 106 and conduit 104 increase in relation to that of the valve 112, the pressure measured at the pressure transducer 118 becomes increasingly biased toward the ambient air. During impaired operation, the pressure as measured drops and recovers more steeply than during normal operation. An offset value 214 that is much larger than the normal offset value 216 is needed to achieve the target pressure. Consequently, an abnormally large offset value can be taken as an index of a partially clogged filter.

Figure 3:
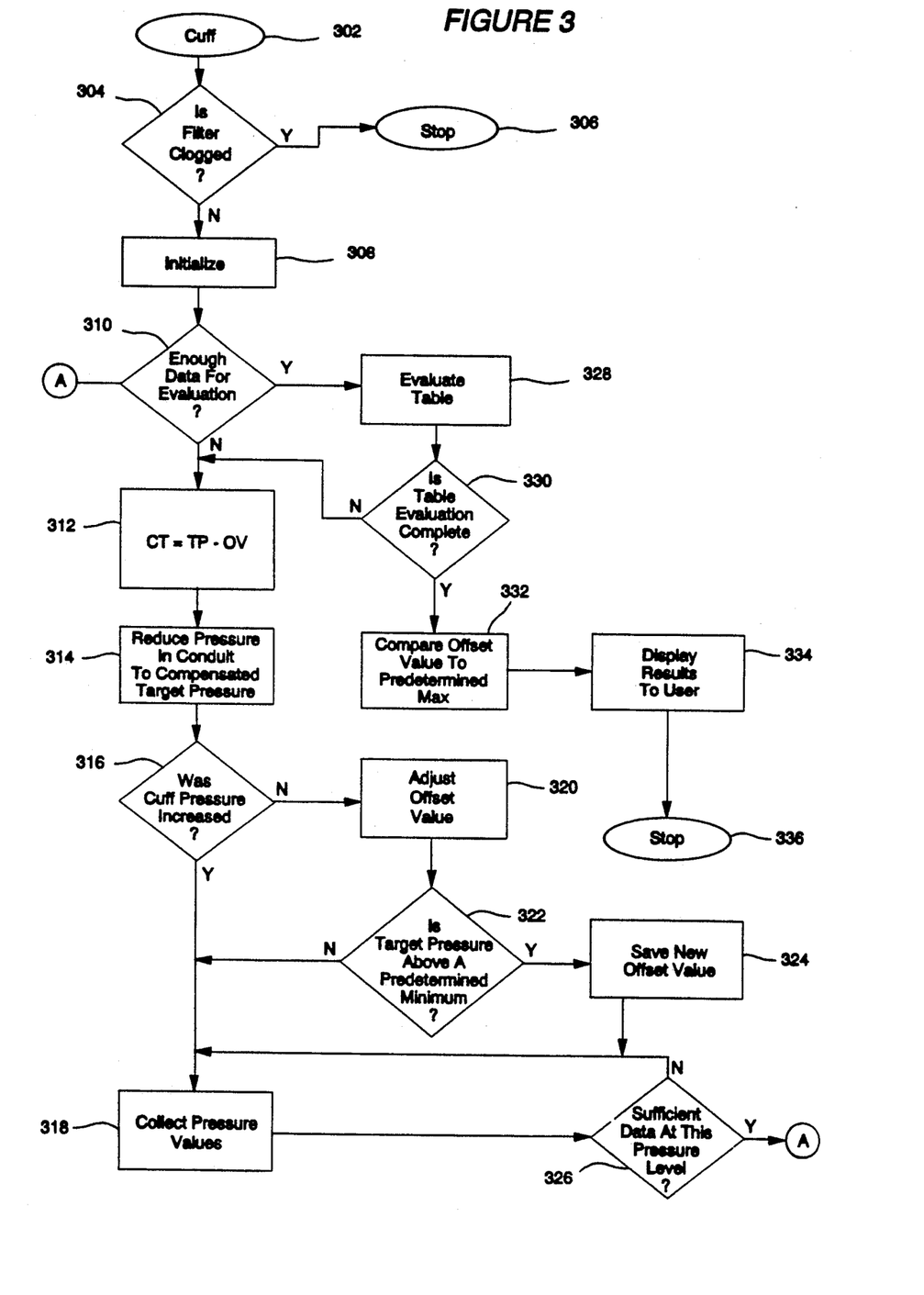
FIG. 3 is a decision flow diagram illustrating a method for operating the automatic blood pressure measuring device of FIG. 1.

The offset value that is used by the fluid pressure controller 116 is initially determined and continuously updated in accordance with the method illustrated by the flow diagram of FIG. 3. Referring to FIG. 3, after the system is initially turned on by a user, step 302, the fluid pressure controller 116 examines a status flag to determine if the filter 106 is clogged, step 304. The status flag is set by the fluid pressure controller 116 any time a determination is made that the filter 106 is clogged. The method by which the determination is made that the filter 106 is clogged, and the status flag is set, will be described in more detail below. Initially, the filter will be considered clogged only of the status flag is set during a prior operation of the blood pressure measuring device 100. In that case, the fluid pressure controller 116 would stop the measurement, step 306, and provide a message to the user to indicate that the measurement cannot be made and the system needs to be serviced.

If the filter 106 is not clogged, then the fluid pressure controller will initialize all other variables, inputs, outputs, flags, etc., for performing the blood pressure measurement, step 308. Particularly, a pressure table will be established by the fluid pressure controller 116 for recording the steady state pressure of the conduit 108 and the oscillometric pressure of the conduit 108 at each incremental pressure supplied to the cuff 102. The pressure table is used for determining the blood pressure of the user by techniques known in the art. In accordance with the subject invention, the steady state pressures are used to determine the offset value as will be discussed below.

After the blood pressure measuring device 100 has been initialized, the fluid pressure controller 116 determines whether enough data has been collected to evaluate the pressure table for determining the blood pressure of the patient, step 310. Generally, the blood pressure table will only be evaluated if a sufficient number of measurements have been taken to identify systole and diastole of the user and the pressure of the cuff is less than 80 mm. Other rules for determining when sufficient data exists to evaluate the blood pressure of the user are known to those skilled in the art and may be readily incorporated and/or substituted for use with the subject invention. If the pressure table contains enough data, it will be evaluated as will be described in more detail below. If not, the fluid pressure controller 116 will calculate a compensated target pressure (CT) as equal to the target pressure (TP) minus the offset value (OV), step 312. As will become apparent to those skilled in the art, only a limited number of times will there be no offset value previously recorded for use in this step. For these times, the offset value can be selected at a default or zero value.

After the compensated target value is selected, the fluid pressure signal is varied to reduce the pressure in the conduit 108 toward the compensated target pressure, step 314. As discussed above, the data processor 116 will vary the fluid pressure signal to stop changing the pressure when the pressure in the conduit 108 equals the compensated target pressure. Since the offset value is selected to compensate for the resistance of the pneumatic system, the final pressure of the cuff 102, after the pressure in the pneumatic system 101 stabilizes, will be equal to the target pressure.

The data processor 116 determines whether the pressure in the cuff 102 was increased, step 316, and if so, the fluid pressure controller 116 will collect value for the steady state pressure and the oscillometric pressure of the conduit 108, step 318. If the change was to decrease the cuff pressure, step 316, then the fluid pressure controller 116 will update the value for the offset by determining the difference between the target pressure and the actual steady state pressure measured by the pressure transducer 118, step 320. More particularly, the new offset value ($OV_n$) will be equal to the old offset value ($OV_o$), plus the difference between the actual pressure (AP) and the target pressure (TP);

$$OV_n = OV_o + (AP - TP)$$

The target pressure is then compared to a predetermined minimum pressure for calculating the offset value, step 322. It has been determined that it is preferable to adjust the offset value only if the pressure in the pneumatic system 101 is above a minimum pressure. In a presently preferred embodiment of the invention, the minimum pressure for determining the offset value is 80 mm. If the target pressure exceeds the predetermined minimum, then the new offset value is saved for use at the next pressure increment, step 324. If the target pressure is not above the predetermined minimum amount, then the new offset value is discarded.

After the offset value has been determined, the fluid pressure controller 116 will collect pressure values until sufficient data has been collected to evaluate the oscillometric pressure of the user at the applied cuff pressure, steps 318 and 326. When sufficient data has been collected the oscillometric pressure of the user will be stored in the pressure table and the fluid pressure controller 116 will again determine whether enough data has been collected to evaluate the pressure table, step 310. If not, the data processor will continue to decrease the pressure of the cuff 102, update the offset value if above the predetermined minimum cuff pressure, and collect data for the pressure table, until the blood pressure measurement calculation can be performed. When enough data has been collected to evaluate the pressure tables, the fluid pressure controller 116 will attempt to evaluate the pressure tables, step 328, to determine the blood pressure of the user. If the tables do not have enough information to determine the blood pressure of the user, then the fluid pressure controller will repeat steps 310-328 until the evaluation of the tables are complete, step 330.

When the blood pressure evaluation and measurement is complete, the data processor 116 will compare the stored offset value to a predetermined maximum value to determine whether the filter is clogged, step 332. It will be apparent to those skilled in the art that when the pressure of the cuff is decreasing, large positive offset values will be indicative of large resistances in the pneumatic system 101. Conversely, for blood pressure measuring devices wherein the pressure of the cuff 102 is incrementally increased, large negative offset values will be indicative of high resistance in the pneumatic system 101. In either event, an extremely high resistance in the pneumatic system 101 indicates that dirt, dust, and other debris may be substantially clogging the filter 106. Accordingly, the fluid pressure controller 116 will determine whether the offset value is above a predetermined maximum, step 332, and if so, will set the status flag to indicate that the filter 106 is clogged, as discussed above by reference to step 304. Thereafter, the fluid system controller will display an error condition to the user, step 334, and will not allow further measurements.

It will be apparent to those skilled in the art, that the method for operating the blood pressure measuring device 100 described herein by reference to FIG. 3 is best suited for a blood pressure measuring device employing a filter 106 for trapping dirt, dust, and other debris. When such a filter is clogged, the resistance of the pneumatic system 101 will increase substantially, thereby requiring the use of the method described above to determine offset values and to ensure accurate blood pressure measurements. Further, the above described method provides a quick and easy way to determine when the filter 106 is clogged sufficiently to require maintenance. However, it should be apparent to those skilled in the art that the method described herein by reference to FIG. 3 may be used with blood pressure measuring devices that do not employ a filter, but nonetheless, include resistance in the pneumatic system 101.

Figure 4A:
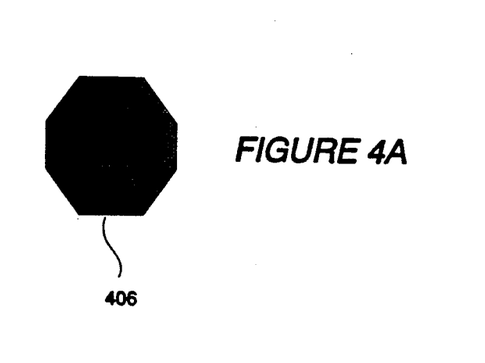
FIGS. 4A, 4B, and 4C are diagrams illustrating a filter for use with an automatic blood pressure measuring device.
Figure 4B:
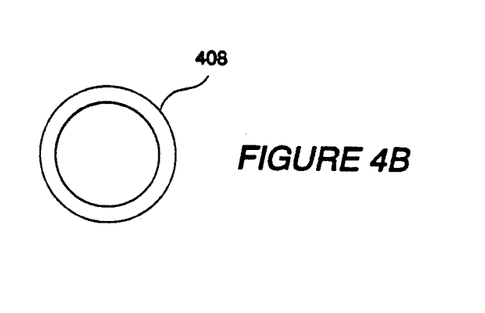
Figure 4C:
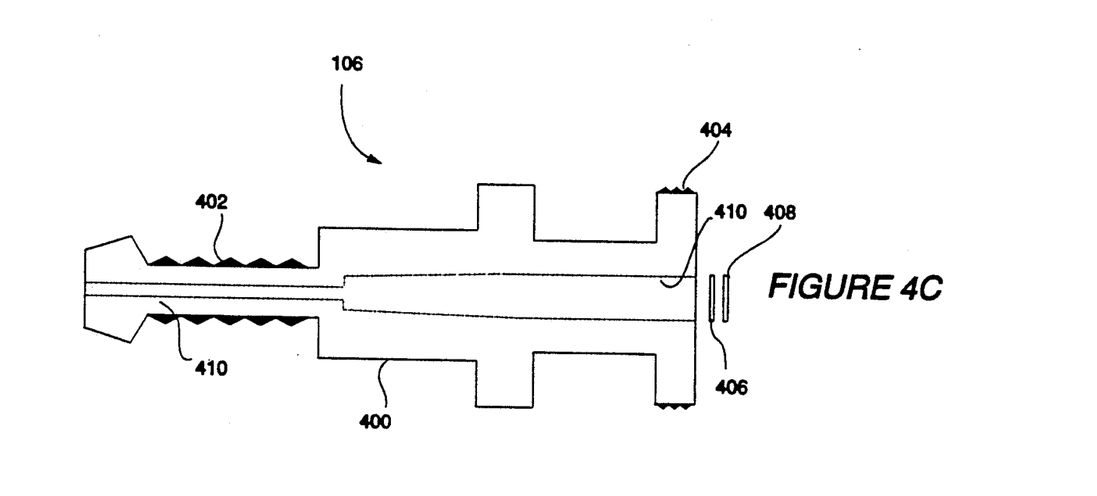

A more detailed illustrative drawing of a filter 106 for use with the present invention is provided in the diagrams of FIGS. 4A, 4B, and 4C. The filter 106, FIG. 4C, comprises a conventional Luer connector 400 that includes a first end 402 constructed for engaging the conduit 104 to securely receive the conduit thereon. The connector 400 includes a second end 404 constructed to engage the conduit 108 and securely receive the conduit 108. The filter also includes a wire cloth 406 (FIG. 4A) and a vinyl grommet 408 (FIG. 4B) that are constructed to be securely mated within a conduit 410 (shown in dotted outline) extending through the connector 400. The wire cloth 406 is constructed of a standard grade wire cloth sufficient to trap all particles that have a size great enough to cause a malfunction of the pneumatic system 100 and/or the fluid pressure assembly 110. Further, it is desired to select the wire cloth 406 of size large enough so that the air flow between the conduit 108 and the cuff 102 is not significantly affected.

The retaining grommet 407 is designed to acquire a tight fit in the retaining conduit 410 to secure the wire cloth 406 therein. The grommet is preferably constructed so that all air passing through the filter 106 goes through the wire cloth 406. Further, it is desired that the grommet 408 not significantly affect the flow of air between the conduit 108 and the cuff 102. In a presently preferred embodiment of the invention, the grommet 408 is made of a vinyl material. However, those skilled in the art will appreciate that the grommet may be made of other materials.

From the foregoing it will be appreciated that, although a specified embodiment of the invention has been described herein for purposes of illustration, various modifications may be made without deviating from the spirit and scope of the invention. Accordingly, the invention is not limited except as by the appended claims.

I claim:

1. A blood pressure measuring device for use with a user's body, wherein the user's body has a flow of blood and wherein the flow of blood has a blood pressure associated therewith, said blood pressure measuring device being constructed for automatically measuring the blood pressure of the flow of blood, said blood pressure measuring device comprising:

fluid pressure means responsive to a control pressure signal for providing a fluid at a selectable pressure, the selectable pressure being increased and decreased by varying the control pressure signal;

inflatable cuff means constructed to be placed upon the user's body for selectively restricting the flow of blood in the user's body, said inflatable cuff means being coupled to receive the fluid provided by said fluid pressure means and to inflate and deflate with respective increases and decreases in the selectable pressure so that the amount of restriction to the flow of blood is varied by variation in the selectable pressure;

fluid conducting means for conducting the fluid from said fluid pressure means to said inflatable cuff means, said fluid conducting means having a first portion and a second portion, said first portion being coupled to said inflatable cuff means and said second portion being coupled to said fluid pressure means;

pressure measurement means coupled to said second portion of said fluid conducting means for providing a response pressure signal indicative of a pressure of the fluid in said fluid conducting means;

fluid filter means coupled intermediate said first and second portions of said fluid conducting means for filtering the fluid to prevent particles of a predetermined size from passing from said inflatable cuff means to said fluid pressure means and said pressure measurement means; and data processing means responsive to the response pressure signal for determining an offset value by measuring the change of the pressure in said fluid conducting means when said fluid pressure means is not varying the pressure, said data processing means being constructed to combine the offset value with a target value for the desired pressure in said inflatable cuff to provide the control pressure signal.

2. The blood pressure measuring device as recited in claim 1 wherein the blood pressure of the flow of blood has an oscillometric pressure and a steady state pressure associated therewith and wherein said data processing means further comprises first electrical filter means for filtering components of the response pressure signal indicative of the oscillometric pressure in said fluid conducting means to obtain a steady state pressure signal indicative of the steady state pressure of the flow of blood.

3. The blood pressure measuring device as recited in claim 2 wherein said data processing means further comprises second electrical filter means for filtering components of the response pressure signal indicative of the steady state pressure in said fluid conducting means to obtain an oscillometric pressure signal indicative of the oscillometric pressure of the flow of blood.

4. The blood pressure measuring device as recited in claim 1 wherein the blood pressure measuring device is operated by a user and wherein said data processing means further comprises a user interface for providing information to the user, said data processing means being further constructed for determining whether the offset value is greater than a predetermined maximum amount and, if so, providing an indication to the user that said fluid filter means is clogged.

5. The blood pressure measuring device as recited in claim 1 wherein said data processing means further comprises memory means for storing the offset value, said data processing means being constructed to store the offset value if the pressure in said fluid conducting means at which the offset value is determined is above a predetermined minimum value.

6. The blood pressure measuring device as recited in claim 1 wherein the control pressure signal includes a pump signal and a valve signal and wherein said fluid pressure means comprises:

an air pump responsive to the pump signal for supplying air to said fluid conducting means to increase the pressure of fluid in said fluid conducting means and said inflatable cuff means; and an air valve responsive to the valve signal for enabling air to escape from said fluid conducting means to decrease the pressure of fluid in said fluid conducting means and said inflatable cuff means.

7. The blood pressure measuring device as recited in claim 1 wherein said fluid conducting means comprises first conduit means for conducting fluid between said fluid pressure means and said fluid filter means and second conduit means for conducting fluid between said fluid filter means and said inflatable cuff.

8. The blood pressure measuring device as recited in claim 1 wherein said fluid filter means comprises:

connector means having a first end for coupling said fluid filter means to said first portion of said fluid conducting means, a second end for coupling said connector means to said second portion of said fluid conducting means, and a fluid channel extending from said first end to said second end for conducting fluid between said first and second portions of said fluid conducting means;

a screen filter constructed of a size to fit within said fluid channel of said connector means; and a grommet constructed of a size to fit within said fluid channel of said connector means, said screen filter and said grommet being secured in said fluid channel proximate said first end for removing debris from the fluid conducted between said first and second conduit means.

9. A blood pressure measuring device for a user's body wherein the user's body has a flow of blood and wherein the flow of blood has a blood pressure associated therewith, the blood pressure measuring device for automatically measuring the blood pressure of the flow of blood, the blood pressure measuring device comprising:

fluid pressure means responsive to a control pressure signal for providing a fluid at a selectable pressure, the selectable pressure being increased and decreased by varying the control pressure signal;

inflatable cuff means constructed to be placed upon the user's body for selectively restricting the flow of blood in the user's body, said inflatable cuff means being coupled to receive the fluid provided by said fluid pressure means and to inflate and deflate with respective increases and decreases in the selectable pressure so that the amount of restriction to the flow of blood is varied by variation in the selectable pressure;

fluid conducting means for conducting the fluid from said pressure measurement means to said inflatable cuff means;

pressure measurement means coupled to said fluid conducting means for providing a pressure signal indicative of the oscillometric pressure of the fluid in said fluid conducting means;

fluid filter means coupled to said fluid conducting means for filtering the fluid to prevent particles of a predetermined size from passing from said inflatable cuff means to said fluid pressure means and said pressure measurement means, said fluid conducting means having a first portion and a second portion, said first portion being coupled to said inflatable cuff means and said second portion being coupled to said fluid pressure means; and data processing means for providing the control pressure signal to incrementally vary the pressure in said inflatable cuff and for determining the oscillometric pressure of said fluid conducting means at each variation to store a plurality of oscillometric pressure values, said data processing means being constructed to process the stored plurality of oscillometric pressure values to determine the blood pressure of the user.

10. The automatic blood pressure measuring device as recited in claim 9 wherein said fluid filter means further comprises:

connector means having a first end for coupling said fluid filter means to said first portion of said fluid conducting means, a second end for coupling said connector means to said second portion of said fluid conducting means, and a fluid channel extending from said first end to said second end for conducting fluid between said first and second portions of said fluid conducting means;

a screen filter constructed of a size to fit within said fluid channel of said connector means; and a grommet constructed of a size of fit within said fluid channel of said connector means, said screen filter and said grommet being secured in said fluid channel proximate said first end for removing debris from the fluid conducted between said first and second conduit means.

11. A method for controlling an automatic blood pressure measuring device including an inflatable cuff, a fluid pressure assembly responsive to a control pressure signal for providing a fluid wherein the fluid has a pressure associated therewith and wherein the pressure of the fluid has a steady state pressure associated therewith, a fluid conducting system for conducting fluid from the fluid pressure assembly to the inflatable cuff, and a filter for filtering fluid conducted from the fluid pressure assembly to the inflatable cuff, said method comprising the steps of:

(a) determining a target pressure to which the pressure of the fluid in the cuff is to be changed;

(b) determining a compensated target pressure equal to the target pressure combined with an offset value;

(c) varying the control pressure signal to change the pressure of the fluid in the fluid conducting system to the compensated target pressure;

(d) sensing a steady state pressure of the fluid in the fluid conducting system after the fluid pressure signal has been varied;

(e) determining the offset value equal to the difference between the steady state pressure of the fluid in the fluid conducting system and the compensated target pressure;

(f) comparing the offset value to a predetermined maximum value and, if the offset value exceeds the predetermined maximum value performing step (g); and (g) providing an indication to the user that the filter of the automatic blood pressure measuring device is clogged.

12. The method as recited in claim 11 wherein step (c), varying the control pressure signal to change the pressure of the fluid in the fluid conducting system further comprises the substeps of:

(h) sensing the pressure of the fluid in the fluid conducting system; and (i) varying the control pressure signal to vary the pressure of the fluid in the fluid conducting system until the pressure sensed in the fluid conducting system equals the compensated target pressure.

13. The method as recited in claim 12 wherein the offset value is stored in a memory, said method further comprising the substeps of:

(j) comparing the pressure of the fluid in the fluid conducting system to a predetermined minimum value and if the pressure of the fluid is below the predetermined minimum value discarding the offset value determined in step (e), and if the pressure of the fluid is not below the predetermined minimum value performing step (i); and (k) replacing the offset value stored in memory with the offset value determined in step (e).

* * * * *

UNITED STATES PATENT AND TRADEMARK OFFICE
CERTIFICATE OF CORRECTION

PATENT NO. : 5,277,187
DATED : January 11, 1994
INVENTOR(S) : Terrance L. Pillsbury It is certified that error appears in the above-identified patent and that said Letters Patent is hereby corrected as shown below:

In column 12, claim 10, line 5, after "size" and before "fit", please delete "of" and substitute therefor --to--.

Signed and Sealed this

Fifth Day of July, 1994

Attest:

BRUCE LEHMAN

Attesting Officer     Commissioner of Patents and Trademarks